United States Patent [19]

Kupchan et al.

[11] 4,005,108
[45] Jan. 25, 1977

[54] NOVEL ANTI-LEUKEMIC DITERPENOID TRIEPOXIDES

[75] Inventors: S. Morris Kupchan, Charlottesville, Va.; William A. Court, Delhi, Canada

[73] Assignee: Research Corporation, New York, N.Y.

[22] Filed: Apr. 3, 1973

[21] Appl. No.: 347,599

[52] U.S. Cl. .......................... 260/343.3 R; 424/279
[51] Int. Cl.² ........................................ C07D 493/22
[58] Field of Search ................................ 260/343.3

[56] References Cited
UNITED STATES PATENTS 3,556,709  9/1963  Evans et al. .................... 260/343.3

OTHER PUBLICATIONS

Kupchan et al., *Tumor Inhibitors*, J.A.C.S. 1972, 94(20), 7194–7195.

*Primary Examiner*—Natalie Trousof
*Assistant Examiner*—C. M. S. Jaisle
*Attorney, Agent, or Firm*—Behr & Woodbridge

[57] ABSTRACT

There are provided novel diterpenoid triepoxides, derived from *Tripterygium wilfordii* Hook F. which possess high and surprising antileukemic activity at dosage levels of micrograms/kilogram body weight.

4 Claims, No Drawings

NOVEL ANTI-LEUKEMIC DITERPENOID TRIEPOXIDES leukemic activity in the microgram/kilogram level, the level at which toxicity is not a significant consideration.

FIG. 1 showing the extraction steps is as follows:

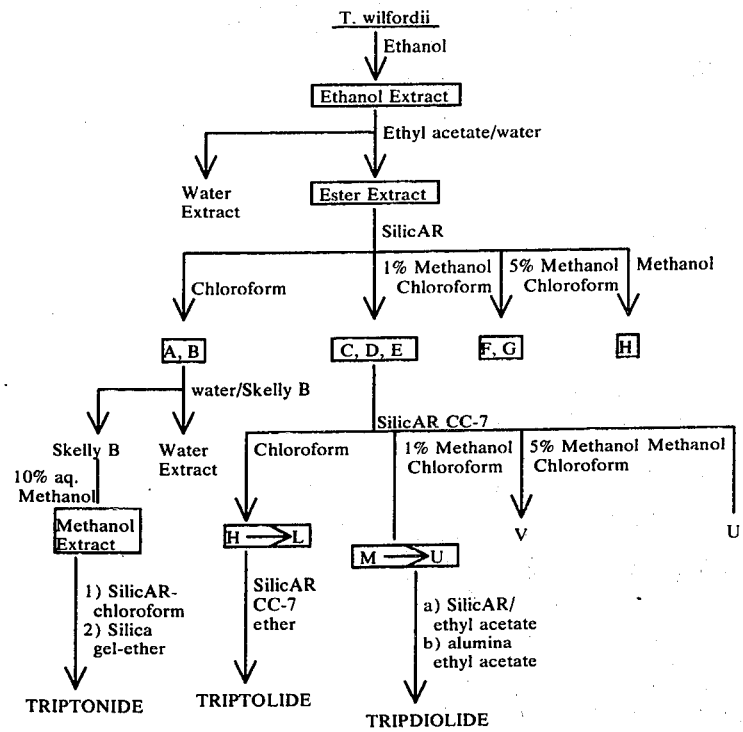

The invention described herein was made in the course of work under grant or award from the Department of Health, Education and Welfare.

SUMMARY OF THE INVENTION

Ethanolic extracts of *Tripterygium wilfordii* are subjected to a series of extraction, chromatographic and purification steps to yield the diterpenoid triepoxides triptolide and tripdiolide which possess high anti-leukemic activity. The general formula of the compounds is shown below.

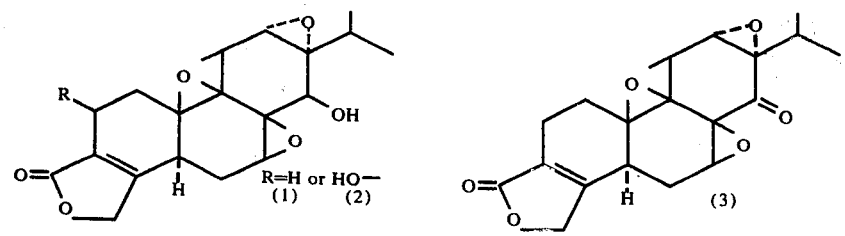

It will be seen that tripdiolide (1) differs from triptolide (2) in the presence of a beta hydroxy group at the 2 position. Triptonide (3) is also isolated.

In the process of isolation the root of *Tripterygium wilfordii* Hook are ground up and extracted with 95% ethanol and subjected to a series of extractions and column fractionations shown and outlined in FIG. I and discussed in greater detail hereinbelow. The active materials isolated were tested for anti-tumor activity in vitro against a standard animal tumor systems recognized in the testing arts. The compounds disclosed and claimed herein demonstrate the significant anti-

DESCRIPTION OF THE PREFERRED EMBODIMENTS

In the process of the present invention dried ground roots of *T. wilfordii* Hook are extracted with several batches of a lower alkanol, suitably ethanol, most preferably 95% ethanol. The extracts combined and the solvent removed, suitably by evaporation, to yield a residue which is then partitioned between a lower alkyl lower alkanoate, suitably ethyl acetate, and water. The aqueous layer is repeatedly washed with the ester solvent combined with the ester layer and the solvent removed, suitably by evaporation to yield a second residue.

The residue from the ester extraction is then subjected to column chromatography on silica gel, suitably on a silicAR type gel. The column is eluted with chloroform, methanol-chloroform and methanol.

The solvent is removed from the chloroform fraction which is then re-chromatographed on silica gel, suitably on silicAR CC-7. Elution with chloroform, methanol-chloroform, and methanol, suitably 1% methanol-chloroform, 5% methanol-chloroform, followed by pure methanol yields a number of fractions.

The chloroform eluate fractions are evaporated and the residues, preferably the residues from the middle fractions are re-chromatographed on silica gel, most suitably on silicAR CC-7. Elution with diethyl ether yields several fractions. Evaporation of the later fractions yields a residue, which, upon crystallization, suitably from methylene chloride/ether, yields triptolide(1).

The later fractions from the 1% methanol-chloroform dilution are combined and re-chromatographed on silica gel, suitably silicAR CC-7 and eluted with ethyl acetate. The second column fraction is separated, evaporated and subjected to thin layer chromatography. In order to obtain pure tripdiolide several successive re-chromatograms are preferred. In each case the middle fraction is selected and recrystallized, suitably from methylene chloride ether to yield tripdiolide (2).

Triptolide and tripdiolide were tested against L-1210 leukemia in mice. The methods used were those set forth in Cancer Chemother. Rep., 25, 1 (1962). In these tests both compounds showed significant in vivo tumor inhibitory activity.

Compounds 1 and 2 showed significant activity against the L-1210 leukemia in a range of 50 to 400 $\mu$g/Kg. Triptolide showed an active range of 80–400 $\mu$g/Kg with optimum activity at about 200 $\mu$g/Kg. Triptolide's range is 50 $\mu$g/Kg – 300 $\mu$g/Kg with optimum response at about 150 $\mu$g/Kg.

The modes contemplated by the inventor of carrying out the invention include pharmaceutical compositions and processes of administration thereof.

Solutions of the principal active ingredient can be prepared in water or in water suitably diluted with, for example, ethanol, glycerin, edible polyols (for example, glycerine, polyethylene glycols, propylene glycol), and the like. Dispersions can be prepared in glycerol, liquid polyethylene glycols, and mixtures thereof, and in oils.

Under ordinary conditions of storage and use, these preparations contain a preservative to prevent the growth of microorganisms.

As stated above, the pharmaceutical compositions can be in forms suited for injectable use which forms include sterile aqueous solutions or dispersions and sterile powders for the extemporaneous preparation of sterile injectable solutions or dispersions. In all cases, the form must be sterile and must be fluid to the extent that easy syringeability exists. It must be stable under the conditions of manufacture and storage must be preserved against the contaminating action of microorganism such as bacteria and fungi. The basic solvent or dispersion medium can contain water, ethanol, polyols (for example, glycerol, propylene, glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersions and by the use of surfactants (for example, a condensation product of ethylene oxide with fatty acids or fatty alcohols, partial esters of fatty acids and a hexitol anhydride, and polyoxethylene condensation products of the esters). The prevention of the action of microorganisms can be brought about by various antibacterial and antifungal agents, for example parabens, chlorobutanol, benzyl alcohol, phenol, sorbic acid, thermerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the principal active ingredient in the required amount in the appropriate solvent with various of the other ingredients enumerated above, as required, followed by filter sterilization. Generally, dispersions are prepared by incorporating the previously sterilized active ingredient into a sterile vehicle which contains the basic dispersion medium and the required other ingredients from those enumerated above.

In the case for sterile powders for the preparation of sterile injectable solutions the preferred method of preparation is the freeze-drying technique which yield a powder of the active ingredient plus any additional desired ingredients from a previously sterile-filtered solution thereof. The powders can also be sterilized by the use of a gas, for example, ethylene oxide and subsequently incorporated, with the required additional ingredients and in the proper particle size, into the basic powder for later reconstitution with the desired suspending liquid which, of course, itself must be sterile.

Supplementary active ingredients can be incorporated into the inventive compositions. These ingredients include for example, mechorethamine hydrochloride and 5-bis (2-chloroethyl) amino-uracil; triethylene melamine; actinomycin C; cycloheximide.

It is especially advantageous to formulate the inventive compositions in dosage unit form for ease of administration and uniformity of dosage. Dosage unit form as used in the specification and claims herein refers to physically discrete units suited as unitary dosages for the animal and human subjects to be treated, each unit containing a predetermined quantity of active material calculated to produce the desired therapeutic effect in association with the required pharmaceutical carrier. The specifications for the novel dosage unit forms of this invention are dictated by and directly dependent of (a) the unique characteristics of the active material and the particular therapeutic effect to be achieved and (b) the limitations inherent in the art of compounding such an active material for the treatment of disease in living subjects having a diseased condition in which bodily health is impaired as disclosed in detail in this specification, these being features of the present invention.

The dosage of the principal active ingredient for the treatment of the indicated condition depends on the age, weight, and condition of the subject being treated, the particular condition and its severity, the particular form of the active ingredient and the route of administration. A dose of from about 30–400 $\mu$g/kg or a daily total dose of from about 0.4 to about 5 mg. given singly or in individually smaller doses is deemed suitable.

The principal active ingredient is compounded for convenient and effective administration in effective amounts with a suitable pharmaceutically acceptable carrier in dosage unit form as hereinbefore described. A unit dosage form can contain the principal active ingredient in amounts ranging from about 0.1 to about 5 mg. per unit. Expressed in proportions the active ingredient is present in from about 0.01 to about 0.1% w./v. of the liquid compositions.

If desired, triptonide (3) is reduced to triptolide. As reducing agents there may be employed mild chemical reagents or catalytic hydrogenation. There may be employed sodium borohydride, disiamyl borane in tetrahydrofuran or hydrogen in the presence of Adams catalyst in ethanol.

EXAMPLE I

Extraction and Preliminary Fractionation of *Tripterygium wilfordii*

The ground roots of *T. wilfordii* Hook (2 kg) were extracted successfully for 6, 15, and 24 hours with 8 l. aliquots of 95% ethanol. The extracts were combined and evaporated to give a residue (210 g.) which was partitioned between ethyl acetate (500 ml.) and water (500 ml.). The aqueous layer was repeatedly washed with fresh ethyl acetate (11 × 500 ml.), the washings combined with the ethyl acetate layer and the solvent evaporated to give a second residue (98.6 g.). This residue was dissolved in chloroform (100 ml.) absorbed in vacuo onto silica gelcelite (1:1, 200 g.) and placed on a column of silica gel (70–325 mesh, 1.2 kg) packed in chloroform. Sequential elution with 2.1 l. aliquots of chloroform (× 2), 5% methanol-chloroform (× 3), 10% methanol/chloroform and methanol afforded fractions A–G respectively.

Column chromatography of the combined fractions C, D, and E (20 g.) on SilicAR CC-7 (75–325 mesh, 2 kg) eluted with successive volumes (2.5 l) of chloroform (× 5), 1% methanol-chloroform (× 9), 5% methanol/chloroform, and methanol afforded fractions H–W respectively.

EXAMPLE II

Isolation of Triptolide

Column chromatography of fraction I (2.7 g) on SilicAR CC07 (75-325 mesh, 2.70 g) eluted with successive volumes (11.5 l.) of diethyl ether yielded seven fractions. Evaporation of the sixth fraction gave a residue (34 mg) crystallization of which from methylene chloride-ether yielded triptolide (21. mg). $C_{20}H_{24}O_6$; mp 226°–228°; $[\alpha]^{25}D - 154°$ (c 0.369, $CH_2Cl_2$); uv max (EtOH) 218 mm ($\epsilon$ 14,000); ir (KBr) 2.89, 5.64, 5.93, 8.05, 8.52 $\mu$; mass spectrum m/e 360.1600 ($M^+$) (calcd, 360.1573); nmr ($CDCl_3$) $\tau$9.03 (3H, $d$, $J_{15,16}=7$ Hz, 16—$CH_3$), 8.90 (3 H, $d$, $J_{15,17} = 7$ Hz, 17—$CH_3$), 8.78 (3 H, s, 20—$CH_3$), 7.17 (1 H, d, J = 11 Hz, OH), 6.54 (1 H, d, $J_{6a,7}= 5$ Hz, 7—H), 6.48 (1 H, $d$ of $d$, J = 11 HZ, $J_{12,14} = 1$ Hz, 14—H), 640 (1 H, $d$ of $d$, $J_{11,12} = 3$ Hz, $J_{12,14} = 1$ Hz, 12—H), 6.00 (1 H, $d$, $J_{11,12} = 3$ Hz, 11—H), 5.22 (2 H, m, 19—$CH_2$).

The structure and stereochemistry of triptolide (1) were determined by direct X-ray crystallographic analysis. Crystals of triptolide are monoclinic with space group $P2_1$ and $\alpha = 13.420(1)$, $b = 6.256(1)$, and $c = 11.593$ (1)A, and $\beta = 118.09(1)°$. There are two molecules in the unit cell. The intensities of 1071 reflections, measured by counter diffractometry with monochromatic CU K $\alpha$ radiation, were used in the structure analysis. The phase problem was solved by the use of symbolic addition and tangent formula refinement procedures, and the atomic parameters were refined by block-diagonal least-squares methods to give R = 0.078. Isotropic thermal parameters were assumed for all atoms. Of the 24 hydrogen atoms 14 were identified from a final different electrondensity function and included with fixed parameters in the refinement process.

A constant indication of the correct absolute configuration is provided both by the results of Hamilton's R-factor ratio test and by the measurement of intensity differences in selected Friedel pairs of reflections. For parameters corresponding to each of the two possible enantiomeric structures the values of R are 0.0785 and 0.0783, when the anomalous dispersion terms for oxygen are taken into account, suggesting a significant distinction between the two configurations at the 90% confidence level. For the 13 structure amplitudes where the magnitude of the difference between F(hkl) and F(hkl) is calculated to be greatest, the observed differences all have the same sign as expected although the actual numerical agreement is indifferent.

EXAMPLE III

Isolation of Tripdiolide

The combined fractions Q, R, S, and T (4.1 g) were applied to a column of SilicAR CC-7 (75–325 mesh, 420 g) and eluted with successive volumes (500 ml.) of ethyl acetate. Evaporation of the second column fraction afforded a residue (650 mg) which was subjected to preparative thin layer chromatography on Kieselgel (30, 200 × 200 × 0.25 mm plates, Camag) using 10% methanol-chloroform as eluant to yield three fractions [$R_f$ 0.3–014 (60 mg), 0.4–0.6 (216 mg), 0.6–0.8 (275 mg.)]. Material from the intermediate fraction resubjected to preparative thin layer chromatography on silica gel (10, 200 × 200 × 0.5 mm plates, E.M. Reagents) using ethyl acetate (× 2) as eluant to afford three fractions [$R_f$ 0.3–0.5 (37 mg), 0.5–0.6 (155 mg), 0.6–0.8 (7 mg)]. Preparative thin layer chromatography of the $R_f$ 0.5–0.6 fraction on Kieselgel (7, 200 × 200 × 0.25 mm plates, Camag) using ethyl acetate as eluant yielded a further three fractions [$R_f$ 0.3–0.5 (13 mg), 0.5–0.65 (105 mg), 0.65–0.8 (9 mg)]. The $R_f$ 0.5–0.65 fraction was subjected to preparative thin layer chromatography on alumina (5, 200 × 200 × 0.25 mm plates, E.M. Reagents) using methanol-chloroform as eluant to yield one major band (57.5 mg). Crystallization of this material from methylene chloride-ether yielded tridiolide (26 mg). $C_{20}H_{21}O_7$; mp 226°–7°; $[\alpha]^{25}D - 138°$ (c 0.139, $CH_2Cl_2$); uv max 217 nm ($\epsilon$ 11,000); ir (KBr) 2.78, 2.88, 5.63, 5.93 u; mass spectrum (Cl) m/e 377.1621 $(M + 1)^+$ (calcd, 377.1600); nmr ($CDCl_2$) $\tau$8.59 (3 H, s, 20—$CH_3$), 8.24 (1 H, bs, 2—OH), 5.29 (1 H, m, 2—H), 5.14 (1 H, t, J = 1.5 Hz, 19—$CH_2$).

Preparative thin layer chromatography of the mother liquors on alumina (2, 200 × 200 × 0.25 mm plates, E.M. Reagents) using 10% methanol-chloroform as eluant and subsequent crystallization yielded a further 1.1 mg. of tripdiolide.

The postulated structure 2 was confirmed by direct X-ray analysis. Crystals of tripdiolide are isostructural with those of triptolide. The space group is P2 with $a = 13.680(2)$, $b = 6.253(1)$, and $c = 11.864(1)$ A, and $\beta = 119.05(1)°$. Monochromatic Mo K$\alpha$ radiation was used to measure the intensities of 1472 reflections significantly above background. The structure was solved by the direct attribution of the phases for the reflections in troptolide to the corresponding reflections in tripdiolide, and the additional oxygen atom was clearly revealed from a difference electondensity function calculated in this way. The structure was refined in the same way as for triptolide to R = 0.082, with the contributions from 15 identifiable hydrogen atoms included.

EXAMPLE IV

Preparation of Triptonide

Isolation of triptonide fraction B (11 gms) was partitioned between 10° of methanol (100 ml) and Skellysolve B ( 2 × 100 ml). The Skellysolve B layers were washed with 10% aqueous methanol (2 × 100 ml) and the methanol extracts combined and evaporated to give a residue (4.8 mg). Column chromatography of the residue on SilicAR CC-7 (75–325 mesh, 140 gms) eluted with successive volume (350 ml) of chloroform yielded 6 fractions. Evaporation of the 5th fraction gave a residue (0.64 gms) which was subjected to preparative thin layer chromatography on silica gel (5, 200 × 200 × 2 ml, E.M. Reagents) using diethyl ether as eluent to yield 3 fractions [$R_f$ 0.2–0.5 (120 ml), 0.5–0.6 (320 ml), 0.6–0.8 (180 ml.)]. Crystallization of the $R_f$ 0.2–0.5 material from methylene chloride in ether afforded triptonide (3) (20 mg) $C_{20}H_{22}O_6$; mp 251°–252°; $[\alpha]^{25}D$ — 175° (c 0.148, $CH_2Cl_2$); uv max (EtOH) 218 nm ($\epsilon$ 12,000); ir (KBr) 5.63, 5.81, 5.92$\mu$; mass spectrum (CI) m/e 359.1474 (M + 1)$^+$ (calcd, 359.1495); nmr ($CDCl_3$) $\tau$9.01 (3 H, d, $J_{15,16}$ = 7 Hz, 16—$CH_3$), 8.92 (3 H, d, $J_{15,17}$ = Hz, 17—$CH_3$), 8.82 (3 H, s, 20—$CH_3$), 6.50 (1 H, d, $J_{6a,7}$ = 5 HZ, 7—H), 6.08, 5.86 (d, $J_{11,12}$= 3 Hz, 11,12—H), 5.19 (2 H, m, 19—$CH_2$). The characteristics of triptonide, including the molecular weight and carbonyl ir absorption at 5.81 $\mu$, supported the 14-dehydrotriptolide structure 3. The structural assignment was confirmed by oxidation of triptolide (1) with $CrO_3$-pyridine complex in dichloromethane, whereupon triptonide was obtained in excellent yield.

Chromatography of fraction C on SilicAR CC-7 followed by preparative thin layer chromatography on alumina gave tripdiolide (2) (0.001%).

We claim:

1. A compound selected from the group having the formula:

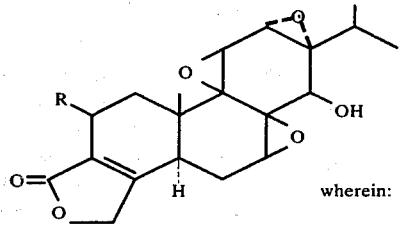

wherein:

R is hydrogen or hydroxy.
2. A compound of claim 1 wherein R is hydrogen.
3. A compound of claim 1 wherein R is hydroxy.
4.

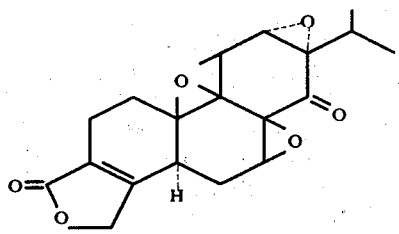

* * * * *